United States Patent [19]

Diesen

[11] Patent Number: 5,300,719
[45] Date of Patent: Apr. 5, 1994

[54] DEHYDROCYCLIZATION OF UNSATURATED HYDROCARBONS TO AROMATIC PRODUCTS

[75] Inventor: Ronald W. Diesen, Midland, Mich.

[73] Assignee: The Dow Chemical Company, Midland, Mich.

[21] Appl. No.: 911,239

[22] Filed: Jul. 9, 1992

[51] Int. Cl.$^5$ .................... C07C 2/76; C07C 5/367
[52] U.S. Cl. .................... 585/417; 585/418; 585/421; 585/435; 585/444
[58] Field of Search ........... 585/430, 417, 434, 421, 585/435, 444

[56] References Cited

U.S. PATENT DOCUMENTS

| | | | |
|---|---|---|---|
| 2,316,271 | 4/1943 | Mattox | 260/668 |
| 2,376,985 | 5/1945 | Voorhees | 260/669 |
| 2,384,984 | 9/1945 | Weizmann | 585/417 |
| 2,392,960 | 1/1946 | Watson | 585/417 |
| 3,207,801 | 9/1965 | Frilette et al. | 260/673.5 |
| 3,546,313 | 12/1970 | Banks | 260/683 |
| 3,830,866 | 8/1974 | D'Alessandro et al. | 260/673 |
| 4,165,441 | 8/1979 | Okano et al. | 585/444 |
| 4,367,358 | 1/1983 | Wideman et al. | 585/440 |
| 4,374,046 | 2/1983 | Antos | 585/660 |
| 4,375,571 | 1/1983 | Hart et al. | 585/431 |
| 5,008,480 | 4/1991 | Slaugh | 585/664 |

FOREIGN PATENT DOCUMENTS 2548428 5/1976 Fed. Rep. of Germany.
552115 3/1946 United Kingdom.

OTHER PUBLICATIONS

Chemical Abstracts, vol. 112, No. 17, Apr. 23, 1990, Columbus, Ohio, U.S.; Abstract No. 157828e, p. 679; JP 1,233,234 (Mitsubishi Kasei Corp.) Sep. 19, 1989.

Suzuka, "Dehydrocyclodimerization of 1,3-Butadiene Catalyzed by Magnesium Oxide and Zirconium Oxide," Applied Catalysis, vol. 47, L7-L8 (1989).

Primary Examiner—Anthony McFarlane
Attorney, Agent, or Firm—Robert M. O'Keefe

[57] ABSTRACT

Aromatic compounds such as ethylbenzene and styrene are produced by contacting butadiene or 4-vinylcyclohexene in a flow reactor with a magnesium oxide, zinc oxide, calcium oxide, strontium oxide, or barium oxide. The products of the process contain low levels of xylene.

10 Claims, No Drawings

DEHYDROCYCLIZATION OF UNSATURATED HYDROCARBONS TO AROMATIC PRODUCTS

BACKGROUND OF THE INVENTION

The present invention relates to methods for converting butadiene to aromatic compounds.

Ethylbenzene is an important commercial solvent and a precursor to styrene. Styrene is a major commercial chemical which finds its principal use in the manufacture of polymers such as polystyrene. Typically, styrene is formed by the dehydrogenation of ethylbenzene. Both ethylbenzene and styrene may be produced by catalytic dehydrocyclization of 4-vinylcyclohexene ("VCH") by use of various known catalysts. Two-step processes for producing styrene and ethylbenzene are also known wherein butadiene is dimerized to form VCH and the VCH is then catalytically aromatized.

However, the prior art lacks methods of producing styrene and ethylbenzene directly from butadiene. Methods for the aromatization of VCH, moreover, have been plagued with poor yields and large amounts of by-products such as xylene with are extremely difficult to separate from the desired products.

For example, Suzuka et al. sealed magnesium oxide and butadiene in a quartz reactor at 200° C. for 17 hours to produce ethylbenzene in a yield of about 17 percent. *Applied Catalysis*, Vol. 47, L7-L8 (1989). However, the major product of the reaction was o-xylene in a yield of about 54 percent.

What is needed are new, more selective and effective processes for the production of aromatics such as ethylbenzene and styrene which alleviate problems in the prior art. What is also needed is a process to produce aromatics directly from butadiene thereby offering a new method of producing the aromatics in one step.

SUMMARY OF INVENTION

This invention, in one respect, is a process to produce ethylbenzene or styrene or mixtures thereof which comprises contacting a moving feedstream containing butadiene or 4-vinylcyclohexene or both with a catalyst in the gas phase under conditions effective to convert at least a portion of the butadiene or 4-vinylcyclohexene or both to ethylbenzene or styrene or mixtures thereof, wherein the catalyst is selected from the group consisting of magnesium oxide, zinc oxide, calcium oxide, strontium oxide, and barium oxide, and wherein the products contain less than 5 mole percent of xylene.

Thus, it has been found that butadiene can be converted to aromatic products such as ethylbenzene and styrene by catalytic aromatization in the presence of certain catalysts. The products formed therefrom have low amounts of by-products and are produced in high yield and high selectivity. The catalysts found effective in these processes include magnesium oxide and zinc oxide.

DETAILED DESCRIPTION OF ILLUSTRATIVE EMBODIMENT

Suitable catalysts of this invention include metal oxides such as magnesium oxide, zinc oxide, calcium oxide, strontium oxide, and barium oxide. The metal oxides can be employed in a variety of physical shapes such as pellets, granules, and spheroids. The metal oxides can be bound with conventional binders such as alumina and silica. In a transport reactor, it is preferred to use a spherically shaped metal oxide. Prior to use, the metal oxide can be calcined using conventional techniques. Preferred metal oxides are magnesium oxide and zinc oxide. Most preferably, the metal oxide is magnesium oxide.

When desired, the catalysts of the present invention can be regenerated by techniques known to those skilled in the art. For example, the catalysts can be regenerated by passing an oxygen-containing gas over the catalyst at elevated temperatures.

The feedstream to be converted in accordance with this invention contains butadiene or VCH or both. The butadiene and VCH need not be 100 percent pure and can contain other hydrocarbons such as alkanes, alkenes, cyclic aliphatics, and aromatics. Thus, this invention is useful for converting butadiene which is found in product streams of crackers, for example, which are utilized widely in industry. The feedstream of this invention can also comprise inert carrier gases such as nitrogen, helium, argon, carbon dioxide, and steam. The feedstream is substantially free of gaseous oxygen with no greater than about 1 percent by volume of the feedstream being gaseous oxygen. A feedstream useful in this invention contains greater than about 10 percent by volume of butadiene or VCH or both. Preferably, the feedstream contains greater than about 20 percent by volume of butadiene or VCH or both.

The process of the present invention is carried out in the gas phase at a temperature in the range from about 400° C. to about 625° C. Preferably, the temperature is from about 450° C. to about 600° C. The pressure can be subatmospheric, atmospheric, or superatmospheric. Preferably the pressure is superatmospheric. When pressure is superatmospheric, it is preferred that pressure be less than about 25 atmospheres, more preferably less than about 10 atmospheres.

The processes of the present invention can be carried out in the gas phase in a variety of flow reactors. Examples of suitable reactors include batch reactors, continuous fixed-bed reactors, fluidized bed reactors, and moving bed reactors. Preferably, the reactor is a continuous flow reactor such as a fixed-bed reactor or is a moving flow reactor such as a falling solids reactor or a riser reactor. The flow rate of feedstream in a continuous flow reactor is expressed as the gas hourly space velocity (GHSV) and is given in units of volume of gaseous feedstream per total reactor volume per hour or simply $hr^{-1}$. The reactor can be operated with a flow rate of reactant in the range from about 100 $hr^{-1}$ to about 36,000 $hr^{-1}$. A more preferred commercial reactor for the process of this invention is a moving bed reactor, such as a riser reactor.

Typically, a riser reactor comprises an upright vessel of relatively low ratio of diameter to length. The catalyst is continuously charged into the bottom of the riser reactor. Likewise, the butadiene feedstream is delivered concurrently to the bottom of the riser reactor as a vapor phase feed or as a liquid phase feed. Preferably, the butadiene feedstream is delivered as a vapor phase feed. The butadiene feedstream moves upward through the reactor, thereby contacting the catalyst. The feedstream and catalyst rise through the reactor and the butadiene is transformed in a single pass to form products of the process. The catalyst is typically separated from the feedstream and products of the process by use of a stripping gas which is delivered to the reactor after the feedstream and catalyst have contacted to produce products. Any conventional stripping gas can be used for this purpose, but VCH is preferred. The product stream exits the riser reactor and is separated by known methods, such as distillation, condensation, adsorption, and zone freezing, to recover the desired products. Unreacted butadiene can be recycled to the riser reactor for further conversion.

The operation of a riser reactor can be simulated by employing a method of alternating pulses of butadiene diluted by an inert gas through a fixed catalyst bed such that the volume ratio of butadiene to catalyst is high. Thus, a pulse of a butadiene feedstream is passed through the catalyst bed wherein the butadiene is converted to products. Next, a pulse of stripper gas is passed through the catalyst bed to purge the bed of residual hydrocarbons. When required, the catalyst can be regenerated by passing an oxygen-containing gas over the catalyst at elevated temperatures. Likewise, in a riser reactor, it is preferred to maintain a high ratio of gas volume to catalyst volume. In other words, a low catalyst loading should be employed in a riser reactor.

When the process of this invention is conducted in a moving bed reactor, described hereinbefore, the flow rate of the reactants can be varied. Generally, in the process of this invention the butadiene feedstream is fed into the reactor at any operable flow rate which promotes the formation of products and yields the desired conversion and selectivity. Preferably, the flow rate of the feedstream in the moving bed reactor is about 100 $hr^{-1}$ to about 20,000 $hr^{-1}$. It should be understood that the space velocity controls the residence time of the reactants. Residence times suitable in the practice of this invention are from about one-half second to 10 seconds, preferably from about 1 to 10 seconds. Desirable residence times are inversely related to pressure. Thus, as pressure in the reactor is increased, the more preferable residence time is lowered. The most desirable residence times are readily determined by a skilled artisan depending on the pressure in the reactor as well as other process conditions.

The process of the present invention converts butadiene feedstream to ethylbenzene and styrene with no greater than about 5 weight percent of the products being xylene. Preferably, the amount of xylene in the product is less than about 4, more preferably less than about 3. In addition to ethylbenzene and styrene, the product stream can contain other aromatics such as benzene and toluene as well as by-products of various types. For example, small quantities of cracking products, such as propylene and ethylene, can be formed. The amount of by-products formed is typically low.

For the purposes of this invention, "conversion" is defined as the mole percentage of butadiene or VCH lost from the feedstream as a result of reaction. The conversion can vary widely depending upon the reactants, the form of the catalyst, and the process conditions such as temperature, pressure, flow rate, and catalyst residence time. Within the preferred temperature range, as the temperature increases the conversion generally increases. Within the preferred gas hourly space velocity range, as the space velocity increases the conversion generally decreases. Typically, the conversion of butadiene or VCH is at least about 10 mole percent. Preferably, the conversion is at least about 20 mole percent; more preferably, at least about 30 mole percent; even more preferably, at least about 40 mole percent; and most preferably, at least about 50 mole percent.

Likewise, for the purposes of this invention "selectivity" is defined as the mole percentage of converted butadiene which forms ethylbenzene or styrene or both. Generally, selectivities also vary widely depending upon the reactants, the form of the catalyst, and the process conditions. Typically, the process of this invention achieves high selectivities to ethylbenzene or styrene or both. Within the preferred temperature range, as the temperature increases the selectivity generally decreases. Within the preferred space velocity range, as the space velocity increases the selectivity generally increases. Typically, the selectivity to ethylbenzene or styrene or both is at least about 40 mole percent. Preferably, the selectivity to ethylbenzene or styrene or both is at least about 50 mole percent, more preferably at least about 60 mole percent, most preferably at least about 70 mole percent.

The concept of simultaneous high conversion and high selectivity can be conveniently expressed in terms of yield. For the purposes of this invention, the term "yield" refers to the numerical product of the single-pass conversion and selectivity. For example, a process according to the present invention operating at a conversion of 0.65, or 65 mole percent, and a selectivity of 0.75, or 75 mole percent, would have a yield of 0.49, or 49 mole percent. Typically, the yield achieved in the process of this invention is at least about 8 mole percent. Preferably, the yield achieved in the process of this invention is at least about 18 mole percent, more preferably at least about 28 mole percent, most preferably at least about 35 mole percent.

Subsequent to aromatization of at least a portion of the feedstream, the aromatized products can be separated and recovered by conventional techniques. The products and remainder of the feedstream are, for instance, continuously separated from the catalyst in a fixed bed reactor by gas movement through the catalyst bed. In the case of a riser reactor, the separation is accomplished by a stripping gas such as VCH charged counter current to the falling catalyst. For example, the product can be condensed to form a liquid and residual butadiene can be removed by vacuum or distillation. Recovered butadiene can be recycled to the reactor, thus facilitating very high conversions of unsaturated hydrocarbons of up to 100 percent.

The following examples are given to illustrate the invention and should not be construed as limiting its scope. All parts and percentages are by weight unless otherwise indicated.

EXAMPLE 1

Conversion of Butadiene to Ethylbenzene Using Magnesium Oxide

A ¼ inch cylindrical steel reactor having a concentric ⅛ inch thermocouple well is filled with 3.9 grams of MgO chips as a catalyst. The reactor is placed in an aluminum block heater with a temperature controller. The reactor void space in the heated zone is about 8 cubic centimeters. The feed composition and the products of reaction are measured with an on-line gas chromatograph through heated sample lines. The MgO chips are made from compressed wafers. The surface area of the MgO catalyst is about 180 square meters per gram. For a feedstream of 38 mole percent butadiene in nitrogen, 15 psig, and a gas hourly space velocity of 190 $hr^{-1}$, a conversion of 18 percent is observed at 450° C. The selectivity to ethylbenzene is 70 percent with benzene and VCH being major by-products. Yield of ethylbenzene is 12.6 percent. Butenes are formed as minor products. No styrene is observed under these conditions.

EXAMPLE 2

Conversion of Butadiene to Aromatics Using Magnesium Oxide

The procedure of Example 1 is repeated in a similar quartz reactor except that the temperature is about 560° C., the gas hourly space velocity is 1500 hr$^{-1}$ in a one minute pulse, and 2 grams of MgO is used and the feedstream is a pulsed feedstream comprising 21 mole percent butadiene in nitrogen. Conversion of about 19 percent is achieved. Selectivities are as follows: ethylbenzene, 48 mole percent; styrene, 12 mole percent; butene, 12 mole percent; benzene, 6 mole percent; VCH, 6 mole percent; toluene, 5 mole percent; and unknowns, 11 mole percent. The total yield of styrene and ethylbenzene is 11 mole percent.

EXAMPLE 3

Conversion of Butadiene to Styrene and Ethylbenzene Using Zinc Oxide

The procedure of Example 1 is repeated except zinc oxide is the catalyst in an amount of 3.5 grams. The gas hourly space velocity is 120 hr$^{-1}$. At 450° C. the butadiene conversion is about 20 percent. Selectivities are as follows: ethylbenzene, 60 mole percent; styrene, 10 mole percent; butene, 24 mole percent; benzene, 2 mole percent; and VCH, 3 mole percent. The yield of ethylbenzene and styrene is 14 percent. The activity of ZnO decreases more quickly as compared to the MgO catalyst.

What is claimed is:

1. A process to produce ethylbenzene or styrene or mixtures thereof which comprises contacting a moving feedstream containing butadiene or 4-vinylcyclohexene or both with a catalyst in the gas phase under conditions effective to convert at least a portion of the butadiene or 4-vinylcyclohexene or both to ethylbenzene or styrene or mixtures thereof, wherein the catalyst is selected from the group consisting of magnesium oxide and zinc oxide and wherein the products contain less than 5 mole percent of xylene.

2. The process of claim 1 wherein the flow rate of the moving butadiene feedstream has a gas hourly space velocity of from about 100 to about 36,000 hr$^{-1}$.

3. The process of claim 1 wherein the temperature is from about 450° C. to about 600° C.

4. The process of claim 1 wherein the catalyst is magnesium oxide.

5. The process of claim 1 wherein the process is conducted in a fixed bed reactor or a moving bed reactor.

6. The process of claim 1 wherein the selectivity to ethylbenzene or styrene or both is at least about 50 mole percent.

7. The process of claim 1 wherein the products contain less than 3 mole percent of xylene.

8. The process of claim 1 wherein the pressure is superatmospheric.

9. The process of claim 7 wherein the pressure is less than about 10 atmospheres.

10. The process of claim 1 wherein residence time of the butadiene is from about 1 second to about 10 seconds.

* * * * *